United States Patent [19]
Zhao

[11] Patent Number: 6,164,281
[45] Date of Patent: Dec. 26, 2000

[54] METHOD OF MAKING AND/OR TREATING DISEASES CHARACTERIZED BY NEOVASCULARIZATION

[76] Inventor: Iris Ginron Zhao, 20 S. 36th St., #520, Philadelphia, Pa. 19104

[21] Appl. No.: 09/119,189

[22] Filed: Jul. 20, 1998

[51] Int. Cl.[7] .................................................. A61B 19/00
[52] U.S. Cl. ........................................... 128/898; 600/301
[58] Field of Search ........................... 128/898; 600/301; 424/94.5; 514/337, 399, 396, 422, 425, 508, 912, 423

[56] References Cited

U.S. PATENT DOCUMENTS

| | | | |
|---|---|---|---|
| 4,665,089 | 5/1987 | Siezen et al. | 514/422 |
| 5,134,156 | 7/1992 | Iwaguchi et al. | 514/423 |
| 5,567,417 | 10/1996 | Sasisekharan et al. | 424/694.5 |
| 5,624,895 | 4/1997 | Sobel | 514/8 |
| 5,643,937 | 7/1997 | Halperin et al. | 514/399 |
| 5,719,167 | 2/1998 | Doshi et al. | 514/337 |
| 5,766,591 | 6/1998 | Brooks et al. | 424/184.1 |

*Primary Examiner*—V. Millin
*Assistant Examiner*—Kelly O'Hara
*Attorney, Agent, or Firm*—Paul D. Inglesby

[57] ABSTRACT

A novel method for making, preventing and reversing pathologic vessel condition, new vessel growth, and macular edema is disclosed. The invention is partially based on the discovery that accelerated formation of new vessel growth occurs near the adjacent area between grafts and recipient and follows the lead of physical force. Pathologic vessel grafts from deceased patient who has such pathologic vessels are grafted into hamster cheek pouch, making the vessel grafts grow as in situ, and thereof therapeutic regiments are set forth for treating neovascularization, macular edema, and angiogenesis.

12 Claims, No Drawings

METHOD OF MAKING AND/OR TREATING DISEASES CHARACTERIZED BY NEOVASCULARIZATION

STATEMENT REGARDING FEDERALLY SPONSORED RESEARCH OR DEVELOPMENT

Acknowledgment to USC Federally Sponsored Research and Development Program.

CROSS-REFERENCES TO RELATED APPLICATIONS

Not Applicable.

MICROFICHE APPENDIX

Not applicable.

BACKGROUND OF THE INVENTION

1. Technical Field

The disclosure relates to a method of making, preventing, and reversing pathologic vessel condition and new vessel growth.

2. Background Art

Neovascularization, or angiogenesis, is the pathological new vessel growth. These conditions characterized by abnormal neovascularization, include diabetic retinopathy, glaucoma secondary to rubeosis iridio, rheumatoid arthritis, and certain solid cancers. For example, diabetic retinopathy is the leading cause of blindness among working age adults in the United States. Microaneurysms are early signs. Such lesions may be associated with hypertension or AIDS, but most commonly with diabetes. Effects on the kidneys may be indicated by the development of albuminuria, and the effects on the peripheral nervous system by diminished perception of hot or cold, but effects of microaneurysm and hemorrhage on retina may threaten man's vision even before other symptoms could happen (Klein, R and Klein B E K: Diabetic Eye Disease, The Lancet, Vol 350, p197–204, July, 1997). A subset of patients with age related macular degeneration develops subretinal neovascularization, which eventually leads to blindness.

Much research has been focused on preventing the formation of the Diabetic Retinopathy prior to blindness. Several models have been used for the study of diabetic retinopathy, helping a better understanding of the process involved. A major problem of angiogenesis, e.g., diabetic retinopathy, is the hardship of making and treating the progressive behavior of neovascularization.

Streptozotocin treatment is used to affect the pancreatic beta cells, rapidly reducing them until insulin is no longer synthesized in sufficient amounts. The galactosemic model shifts metabolism away from glucose, increasing aldose reductase and retinal polyol metabolism. Finally, two weeks of cycled oxygen from high to low tension every 24 hours, followed by return to room air triggers microangiogenesis in developing retina. Use of these models, separately or in combination, as well as electroretinographic analysis, has begun to reveal the events taking place as diabetic retinopathy progresses. Endothelial cells become separated from pericytes as basement membranes thicken, and vascular endothelial growth factor increases, triggering their proliferation (Bazan N G et al.: Experimental Models and Their Use in Studies of Diabetic Retinal Microangiopathy, Therapie, 52(5): 447–51, 1997 Sep–Oct.). Human neovascularization studies are limited by the inaccessibility of the affected tissues. (Pfeiffer, A. et al: Growth Factor Alterations in Advanced Diabetic Retinopathy: A Possible Role of Blood Retina Barrier Breakdown, Diabetes 46, Suppl 2: S26–S30, 1997). Much research has focused on the galactosemic model of dog eyes. Simulating human diabetic retinopathy angiogenesis and observing the unique human retinal neovascularization progress have been a long existing unsolved problem (Eastman, R C et al.: Model of Complications of NIDDM. 1. Model construction and assumptions, Diabetes Care, 20(5), pp 725–734, May 1997) (Kern T S & Engerman R L: Capillary lesion develop in retinal rather than cerebral cortex in diabetes and experimental galactosemia, Achives of Ophthalmology, 114(3): 306–310, March, 1996).

Also, most cancers can't grow bigger than one to two mm diameter if there is no angiogenesis. It would be desirable to test and identify antiangiogenesis agents useful in treating the foregoing diseases on animals who can host human angiogenesis. This method provides human xenograft neovascularization for exploring the mechanism of angiogenesis and prompt response of pharmaceutical testing.

BRIEF SUMMARY OF THE INVENTION

Not applicable.

BRIEF DESCRIPTION OF THE SEVERAL VIEWS OF THE DRAWINGS

Not applicable.

DETAILED DESCRIPTION OF THE INVENTION

The disclosure is used in connection with making and treating angiogenic condition. As used herein, an angiogenic condition means a disease or undesirable medical condition having a pathology including neovascularization.

Since the cheek pouch tissue is immunologically privileged site, the hamster everted cheek pouch preparation has been used extensively to study the microcirculation of the cheek pouch vessels as well as that of transplanted renal, pituitary and pulmonary tissue. The bigger the difference between the species, the more difficult for the xenograft to survive (Barker, C F and Billingham, R E: J. Exp. Med. 620–639, 1971) (Barker, C F and Billingham, R E: Adv. Immunol. 25: 1–54, 1977)(Handler, A H: Tumor Research, Prog. Exp., 16: 368–369, 1972).

To investigate the morphological characteristic of human tissue, two cancer females and one alcoholism male eye donors were reserved in K-sol for approximately 1 hour at 4° C. and RPMI Medium 1640 with L-Glutamine at 4° C. for approximately 2–4 hours and prepared by 0.55 Trypsin for 10–30 minutes. Four males (body weight 110–130 g) and four females (body weight 150–200 g) Golden Syrian Hamsters were used as recipients. By the 7th day after transplantation, most tissues had reperfused as demonstrated by brisk RBC flow. Microscopy showed the absence of adherence of WBC and proved the acceptance of the graft from normal human eye tissue into hamster cheek pouch. (Chao, J R et al.: Microvascular observation of retinal, choroid and Ciliary body tissue from human grafted into hamster cheek pouch, Federation of American Societies for Experimental Biology, March, 1989).

Improved from previous studies of rejection, the disclosure is a new use of old xenograft technique developed for making and treating angiogenesis, the particular condition is within 3–5 days when the neovascularization is on its peak and majority of blood sprout and whirls have not been sealed. Particular area of neovascularization is in the interface between the recipient and the graft (adjacent area).

To make pathologic vessel condition and neovascularization, human tissue with pathologic new vessel growth can be grafted into Golden Syrian Hamsters or Chinese Crisetulus Griseus Hamsters. Next day after operation, the operation area is full of random blood flows, which can be any direction and resembles blood sinus. Third day to fifth day after operation, the operation area is rich of brick blood flow streams with strong tendency to search for other blood stream until forming a circuit or stopping at the center of a whirl. The most active new vessel formation can be seen at the interface zone between the graft and the recipient (adjacent area), which documents the dynamic leading effect of RBC leakage and an interest mechanism about the formation of neovascularization. The new formed vessels inherit the original pattern of the donor graft. A pathologic condition may be added to facilitate the original progressive behavior. By 7th day after operation, the endothelial cells have grown along the blood stream and sealed the circuit. No clot or obvious rejection line can be noticed around the implant area. It indicates that blood vessels can be a "privileged tissue" because of their low content of HLA. An interesting point that the application suggests is the healing process likely starting from the recipient side, and stabilizing the progress of neovascularization from the graft side and eventually stabilizing the angiogenesis from the recipient side to the graft side. It resembles a benign healing response.

Comparing new vessel growth in a variety of conditions as the following table:

neovascular glaucoma. Present art is also useful when a condition has the additional element of endothelial or vascular smooth muscle cell proliferation that is not necessarily associated with the unwanted new vessel growth, e.g., angioma. In both conditions, the methods of making and treating angiogenesis are in the presence of the precise structure of human vascular diseases and active neovascularization stage.

Differentiated from prior art which used actinonin or its salt as a therapeutic agent for inhibiting angiogenesis in a mammal having diabetic retinopathy or inflammatory response with angiogenesis (U.S. Pat. No. 5,134,156, Pharmaceutical composition and methods for angiogenesis inhibition; U.S. Pat. No. 5,763,441, Actinonin aproteinase inhibitor potentially inhibitors angiogenesis), the disclosure focuses on dynamic controlling of Osm, red blood cell leakage, reducing blood sprouting and whirling. Controlling hypertonic glycemic frustration and reducing the bleeding will reduce endothelial cell growth following the bleeding sprout. Antihemorrhage composition, e.g., fibrinogen and healing process will reduce the numbers and severity of vasculogenesis or angiogenesis.

Generally, it is not expected that hyperglycemia and heparin could lead high molecular weight or red blood cell leaking, and inhibitors of such leakage will inhibit endothelial or vascular proliferation. Thus, the application of hypertonic glycemic stress or heparin perfusion will open the tight junction, gap, and barrier and cause leakage is surprising. Also it is reversible once it is opened. The application means the blood-retinal barrier can be opened and closed. For example, heparin perfusion will cause vessel leaking immediately. The leaking is reversed immediately

|  |  | Diabetic Retinopathy | | |
| --- | --- | --- | --- | --- |
| Condition | Chronic Rejection | Proliferation | Macular Edema | Neovascularization |
| Immune Response | +++ | + | -- | + |
| Healing Process | + | + | -- | + |
| 1–3 day | reperfusion/leaking | leaking | leaking | leaking |
| 3–5 day | neovascularization | neovascularization | edema | neovascularization |
| 5–21 day | neovascularization arrested & accepted | neovascularization | edema | neovascularization arrested & accepted |
| Long term | vessel narrowing vessel occlusion rejection | vessel narrowing vessel occlusion fiber contract | | vessel narrowing vessel occlusion fiber contract |

Even though hamster's blood is flowing in the vessels of human retina graft, the neovascularization is from patients who are aware of what is occurring with their vessels and have volunteered their eyes for the experiment. A selected trace marker can be introduced by injection into the hamster's vessels.

The application includes, but is not limited to xenograft method with or without window or chamber, cycled glycemic frustration from high to low every 6–24 hours, oxygen stimulation method, vein occlusion method, and direct vessel irrigating system. Also, heparin perfusion, AID patient body fluid, many cancer exudation or toxic material can induce severe vessel damage, hemorrhage, or angiogenesis.

Proliferation of endothelial and vascular smooth muscle cells is one main feature of neovascularization. But the goal of the present art is making and testing inhibition of pathological stimulated angiogenesis pattern and, therefore arresting such progression which depends in whole or in part upon such neovascularization, e.g., diabetic retinopathy and iris after removing heparin. Furthermore, aspirin can reduce the platelet aggregation and will accelerate the hemorrhage and consequently the vasculogenesis. Thus aspirin-like agents should be used with special precaution with an angiogenesis condition. In contrast, wound healing and antihemorrhage compositions, or direct dynamic controlling inhibits such neovascularization as shown in the following chart.

TREATING NEOVASCULARIZATION

| Cause of Neovascularization | Treating Regimen |
| --- | --- |
| #1 High Osm, Heparin, Hypertension | #1' isotonic glycemia, water dilution |
| Hypertonic glycemia, harm material or environment, glycation end product ↓ Endothelium shrunk | aldose reductase, aminoguanidine |

-continued

| Cause of Neovascularization | Treating Regimen |
|---|---|
| #2 Junction, gap & barrier open | #2' calcium, heparinase |
| |⊕ Vessel occlusion | |
| |⊕ EDTA, heparin | |
| ↓⊕ Aspirin, low IOP | |
| #3 Protein, RBC leakage | #3' antihemorrhage, high IOP |
| ↓ | |
| #4 Bleeding sprouting or whirling | #4' benign healing inducers |
| ↓⊕ Growth factor | |
| #5 Endothelium growing | #5' chronic immune response |
| | angiostatic compound |
| | growth inhibit factor |
| | anticancer, antifungi, |
| | anticytotoxin |

Prompt removing offending factors, stopping damage, and arresting leakage and hemorrhage are more pertinent than inhibiting endothelium growth by cytotoxin.

The disclosure emphasizes on RBC leakage, blood flow sprouting and accompanied endothelium growing along with the blood flow sprouting. No matter the leaking is caused by hypertonic induced tight junction, gap and barrier opening, hyper or hypoxemia, wound cutting, tumor, inflammation, vein occlusion, toxin, or an inducer, bleeding intends to accumulate in the most loose tissue or recess. The bleeding stream intends to search another blood stream to form an anastomosis to seal the circuit. The shape and direction of the neovascularization is driven by the force and follow the striate of the tissue. Accordingly, the disclosure focuses on the cause and early stage controlling rather than antibiosynthesis agents or cytotoxin. Balanced isotonic solution and perfusion, antihemorrhage composition, tight junction, gap and barrier stabilizer, benign healing composition, or immune agents are preferred.

For example, even though the RBC leakage and endothelium growing along with sprouting and whirling has extended into the recipient side, the combination of healing and rejection agents will inhibit such progression and eventually will stop the neovascularization from the recipient sides to the donor sides. Any one or a mixture of benign wound healing agents, normal antihemorrhage composition, normal humoral antibodies and complements, anticancer or antifungi agents, may bring an optimal prospect regimen of regressing pathological new vasculogenesis to everyone skilled in the art.

In pathologic neovascularization, leakage per se is foreign to surrounding tissue, which will cause inflammation, immune response and wound healing process. Such early response may be beneficial for the host because it will help healing and obliterate the neovascularization. On the other hand, the outcome may be deleterious if it leads to unwanted fibrosis and neovascularization without resolution of the underlying injurious process, e.g., hyperglycemia frustration, hyper or hypoxemia, trauma, toxin, hypertension, or an inducer. Also, the application has no intention to go beyond the benign healing process to a rejection condition, which obliterates new growing vessels first and original vessels eventually.

Unlike normal vessels, the angiogenesis vessel leaking will not cause vasospasm, platelet adhesion, hemostasis, and blood coagulation, or spontaneous arrest of the bleeding sprouting within hours, rather, the leaking will not stop until it meets another blood stream and forms an anastomosis or circuit, or till the endothelium growing and covering the blood stream to seal the leakage, sprouting or whirling. The sealing process takes 3–5 days. Inhibiting the expression of vascular endothelium growth factor may not reduce the underline causes and is not advocated. Heparin binds not only antithrombin but also binds the endothelial cell surface and opens the tight junction, gap and barriers between endothelium. Heparin effect can be reversible and just like hyperosmole shrinks the endothelial cells and causes leaking. After removing the cause, the endothelial cell may recover back to previous shape and maintain the tight junction and gap. Even in the retinal and brain, the tight junction complex and barrier can be opened by heparin and will start to leak. Also the tight junction complex and barrier can be closed only if cell structure and function are intact. Beyond the point, it will not be reversible. For example, surgical pulling may open the barrier permanently.

Since aspirin-like effect inhibits platelet adhesion and aggregation for 8 days until new platelets are formed, discontinuing aspirin, NSAID, vasodilator, calcium binder, warfarin, heparin, and anticoagulation drug during active neovascularization must be emphasized. Sealing leakage needs vasospasm, platelet adhesion, aggregation, thrombosis, coagulation, removing junction, gap and barrier opening agent and underline cause of damage as an intact regimen.

Laser photocoagulation is a sterilized physical treatment for diabetic retinopathy and can be explained by the applicant as a benign healing inducer, which inhibits the progression of leaking and obliterates the microaneurysm. Since the operation and photocoagulation is delicate, expensive, and is usually performed on vulnerable cases, it would be desirable to provide an effective non-surgical treatment either by way of prevention or reversal of the leakage, which leads the neovascularization.

Upon above reasons, a method of making, preventing, and reversing pathologic vessel condition, new vessel growth, or macular edema is set forth as.

a) selecting a tissue from deceased patient who has a pathologic vessel condition, new vessel growth, or macular edema, b) cutting said tissue into small pieces approximately 0.1–5 mm$^2$ by size, or $\leq 1$ mm by thickness, c) selecting and opening a hamster cheek pouch and grafting said tissue pieces into the underdermal loose connective tissue of said hamster cheek pouch and closing said opening by said hamster's skin, d) maintaining b) and c) under sterilized condition, e) maintaining b) and c) in a temperature approximately 1° C. to 24° C., prefer 1° C. to 17° C., f) accelerating neovascularization in the interface between the graft and recipient and the adjacent area, by administering physical stimulation of operation, EDTA treatment, trypsin digestion, cycled glycemia frustration, glycation end product injection, oxygen stimulation, anticoagulation perfusion, heparin treatment, toxin, cancer exudate, AID exudate, or combinations thereof, g) optionally providing a pathologic environment-like condition for facilitating the neovascularization, h) administering a testing material, compound, or angiostatic drug to control pathologic vessel condition, new vessel growth, or macular edema.

Dynamic blood flow or vessel leakage can be monitored by flurorescein angiography, isotope, radioactive, or immune trace marker.

RBC leakage, vessel diameter, or neovascularization can be monitored by inverted microscope, immerse microscope, slit lamp with retrograde or focused illumination, or electronic microscope.

A tested drug can be injected into or perfused on a graft area and their leakage can be measured.

Furthermore, the method comprises monitoring immediate short term inhibition of the drug for decreasing the blood sprouting, whirling, and endothelium growth along with the sprouting and the whirling for arresting neovascularization.

In addition, the method comprises selecting or timing a peak of angiogenesis within 3rd–7th days after the surgery.

Accordingly, a new therapeutic strategy of controlling Osm, stabilizing junction, gap and barrier, and helping healing is set forth as:
  a) gentle pressure maneuver approximately 18–40 mmHg on closed eye lids for about 10 seconds to about 30 minutes for reducing the leaking force,
  b) administering water dilution for reducing hypertonic damage,
  c) administering isotonic control of body fluid and glucose,
  d) administering glycation end product remover,
  e) administering anti-pathologic leakage agent,
  f) administering angiostatic compound for maintaining vessel junction, gap and barrier closed,
  g) reducing eye temperature to approximately 30° C. to 35° C.,
  h) administering benign healing inducer or combinations thereof.

Moreover, such method comprises administering a therapeutic or prophylactically effective amount of a physiologically acceptable compound that protects or reverses the pathologic vessel condition, new vessel growth, or macular edema, being selected from the group of selenium, vitamin E, vitamin P, vitamin C, vitamin A, heparinase, calcium, aminoguanidine, adenosine, inosine, guanosine, aminocaproic acid, adrenobazonum, tranexamic acid, or a mixture thereof.

Furthermore, the method comprises administering a therapeutic or prophylactically effective amount of a physiologically acceptable natural base or herb component, being selected from the group of cirsium japonicum, rumex potientia or crisppus, cogongrass rhizome, imperata rhizome, rhizoma imperatae, imperata cylindrica, gramineae, collicarpa pedunculata, typha angustata, pollen typhae, sanqui sorbaofficinalis, scrophularia ningpaensis, biota ponicum, lycium Chinese, larbarum, white peony root skin, paeonia lactifora, rehmannia glutinosa, panax notoginser, gynura segetum, anemarrhena asphodeloides root, chrysanthemum flower, phellodendron bark, yellow-cork tree bark, cortex phellodendron Chinese, *P. amurense,* rutaceae, siberian solomonseal rhizome, rhizome polygonati, *P. cyrtonema,* liliaceae, polygonatum sibiricum, *P. kingianum,* pueraria lobata, *P. pseudohirsuta,* abalone shell, sea-ear shell, concha haliotidis, rubia cordifolia, lotus root, bletilla striata, fragrant solomonseal rhizome, rhizoma polygonati odoratic, ophiopogon japonicus, red sage root, radix salviae miltiorrhizae, labiatae, berry, or a mixture thereof.

If there is no leaking, there will no new vessel formation. An anti-pathogenic neovascularization regimen, package, or cocktail is a mixture of any one of the link, e.g., removing offending cause, supplementary potentiating agent, antihemorrhage agent, calcium, angiostatic, wound healing inducer, junction, gap and barrier stabilizer, anti-heparin agent, anti-aspirin abuse agent, or anti-hyperglycemia compound. Any agent, when used in cocktails, regimens, or package, is administered in therapeutically effective amounts. A minimum optimal therapeutically effective amount is the amount from minimum to optical level of the agent in the area to effectively stabilizing the angiogenesis, inhibiting neovascularization and controlling the underling cause of damage which constant breaks the tight junction, gap and barrier. The delivery of effective angiostatic compound can be any common administer vehicle, e.g., pill, tablet, implant, oilment, patch, injection solution, eye drop, or irrigating.

Increased intraocular pressure or cold temperature can reduce hemorrhage not only during surgery but also may be an useful maneuver to reduce neovascularization outside the operation room.

Those skilled in the art will be able to ascertain with no more than routine experimentation numerous equivalents to this specific method of making and treating neovascularization. Such equivalents are considered to be within the scope of the invention and are intended to be embraced by the following claims.

What is claimed and desired to be secured by United States Patent is:

1. A method of making, preventing, and reversing pathologic vessel condition, new vessel growth, vessel leakage, or macular edema comprises the steps of:
  a) selecting a tissue from deceased patient who has said pathologic vessel condition, new vessel growth, vessel leakage, or macular edema,
  b) cutting said tissue into small pieces approximately 0.1–5 mm$^2$ by size, or $\leq 1$ mm by thickness,
  c) selecting and opening a hamster cheek pouch, and grafting said tissue pieces into underdermal loose connective tissue of said hamster cheek pouch and closing said opening by said hamster's skin,
  d) maintaining b) and c) under sterilized condition,
  e) maintaining b) and c) in a temperature approximately 1° C. to 24 ° C., prefer 1° C. to 17° C.,
  f) accelerating neovascularization in the interface between the graft and recipient and the adjacent area, by administering physical stimulation of operation, EDTA treatment, trypsin digestion, cycled glycemia frustration, glycation end product injection, oxygen stimulation, anticoagulation perfusion, heparin treatment, toxin, cancer exudate, AID exudate, or combinations thereof,
  g) optionally providing a pathologic environment-like condition for facilitating neovascularization,
  h) administering a testing material, compound, or angiostatic drug to affect neovascularization.

2. The method in accordance with claim 1 further comprises: monitoring dynamic blood flow or leakage by flurorescein angiography.

3. The method in accordance with claim 1 further comprises: monitoring dynamic blood flow or leakage by isotope, radioactive, or immune trace marker.

4. The method in accordance with claim 1 further comprises:
  monitoring the RBC leakage, vessel diameter, or neovascularization by inverted microscope, immerse microscope, slit lamp with retrograde or focused illumination, electronic microscope, or combinations thereof.

5. The method in accordance with claim 1 further comprises:
  injecting a tested drug into a graft area and measuring affected leakage.

6. The method in accordance with claim 1 further comprises:

perfusing a tested drug on a graft area and measuring affected leakage.

7. The method in accordance with claim 1 further comprises:

monitoring immediate or short term inhibition of a test drug for decreasing blood sprouting, whirling, and endothelium growing along with said sprouting and whirling for arresting neovascularization.

8. The method in accordance with claim 1 further comprises:

selecting or timing a peak of angiogenesis within 3rd–7th days after said surgery.

9. The method in accordance with claim 1 wherein the step of preventing or reversing pathologic vessel condition, new vessel growth, or macular edema comprises:

a) gentle pressure maneuver approximately 18–40 mmHg on closed eye lids for about 10 seconds to about 30 minutes for reducing the leaking force, b) administering water dilution for reducing hypertonic damage, c) administering isotonic control of body fluid and glucose, d) administering glycation end product remover, e) administering anti-pathologic leakage agent, f) administering angiostatic compound for maintaining vessel junction, gap and barrier closed, g) reducing eye temperature to approximately 30° C. to 35° C., and h) administering benign healing inducer.

10. The method in accordance with claim 1 wherein the step of preventing or reversing pathologic vessel condition, new vessel growth, or macular edema comprises administering a therapeutic or prophylactically effective amount of a physiologically acceptable compound that protects or reverses pathologic leakage, being selected from the group of selenium, vitamin E, vitamin P, vitamin C, vitamin A, heparinase, calcium, aminoguanidine, adenosine, inosine, guanosine, aminocaproic acid, adrenobazonum, tranexamic acid, or a mixture thereof.

11. The method in accordance with claim 1 wherein the step of preventing or reversing pathologic vessel condition, new vessel growth, or macular edema comprises administering a therapeutic or prophylactically effective amount of a physiologically acceptable natural base or herb component that protects or reverses pathologic leakage, being selected from the group of cirsiumjaponicum, rumex potientia or crisppus, cogongrass rhizome, imperata rhizome, rhizoma imperatae, imperata cylindrica, grarnineae, collicarpa pedunculata, typha angustata, pollen typhae, sanqui sorbaofficinalis, scrophularia ningpaensis, biota ponicum, lycium Chinese, larbarum, white peony root skin, paeonia lactifora, rehmannia glutinosa, panax notoginser, gynura segetum, anemarrhena asphodeloides root, chrysanthemum flower, phellodendron bark, yellow-cork tree bark, cortex phellodendron Chinese, *P. amurense,* rutaceae, siberian solomonseal rhizome, rhizome polygonati, *P. cyrtonema,* liliaceae, polygonatum sibiricum, *P. kingianum,* pueraria lobata, *P. pseudohirsuta,* abalone shell, sea-ear shell, concha haliotidis, rubia cordifolia, lotus root, bletilla striata, fragrant solomonseal rhizome, rhizoma polygonati odoratic, ophiopogon japonicus, red sage root, radix salviae miltiorrhizae, labiatae, berry, or a mixture thereof.

12. The method in accordance with claim 1 further comprises delivering preventing and reversing pathologic leakage compound by a physiologically balanced irrigating solution, a injection solution or an eye drop, an edible pill, a capsule, a tablet, a patch, an oilment, or a mixture thereof.

* * * * *